United States Patent [19]

Davis et al.

[11] Patent Number: 4,989,462
[45] Date of Patent: Feb. 5, 1991

[54] IMPACT SENSOR

[75] Inventors: Michael W. Davis, Prospect; Leonard J. Weiland, Butler; Mark F. Zanella, Zelienople, all of Pa.

[73] Assignee: AGR International, Inc., Butler, Pa.

[21] Appl. No.: 373,570

[22] Filed: Jun. 30, 1989

[51] Int. Cl.$^5$ .................... G01L 5/00; G01P 15/04
[52] U.S. Cl. .................... 73/862.53; 73/12; 73/492
[58] Field of Search .............. 73/11, 12, 492, 493, 73/862.53, 862.54, 866.4; 340/665, 669

[56] References Cited

U.S. PATENT DOCUMENTS

| | | | |
|---|---|---|---|
| 3,020,875 | 2/1962 | Browning | 116/114 |
| 3,021,813 | 2/1962 | Rips | 116/114 |
| 3,149,606 | 9/1964 | Falkner | 116/114 |
| 3,380,294 | 4/1968 | Redmond | 73/82 |
| 4,062,221 | 12/1977 | Oberheide et al. | 73/11 |
| 4,161,874 | 7/1979 | Specker et al. | 73/12 |
| 4,633,703 | 1/1987 | Needleman | 73/11 |
| 4,798,096 | 1/1989 | Bogatzki | 73/12 |
| 4,829,812 | 5/1989 | Parks et al. | 73/12 |
| 4,856,318 | 8/1989 | Hogan et al. | 73/12 |
| 4,873,867 | 10/1989 | McPherson et al. | 73/493 |

FOREIGN PATENT DOCUMENTS 0125429  9/1980  Japan ..................... 73/12

OTHER PUBLICATIONS

"Accelerometer Instruction & Selection Manual", p. 3, Entran International.
"EGA Series Miniature Accelerometers Biaxial and Triaxial", Entran Specification EGA23S-187.
"Impact-o-graph Impact Indicators", Impact-o-graph Division-Chatsworth Data Corporation, Chatsworth, Calif.

Primary Examiner—Charles A. Ruehl
Attorney, Agent, or Firm—Buchanan Ingersoll

[57] ABSTRACT

A housing, simulating the configuration of a container such as a glass bottle, includes an internal chamber for supporting a center post having an axial bore for receiving a biaxial accelerometer electrically connected to circuitry for detecting and recording the magnitude of the impact force applied externally to the housing. In a method for simulating the impact forces applied to glass bottles as they are conveyed in a bottling operation impact forces are applied at any angle to the housing and are transmitted to the accelerometer. The accelerometer is actuated to generate an output signal expressed in terms of the X and Y vectors of the impact force to the electrical circuitry. The output signal is processed to indicate the magnitude of the applied impact force.

20 Claims, 3 Drawing Sheets

IMPACT SENSOR

BACKGROUND OF THE INVENTION

1. Field of the Invention

This invention relates to method and apparatus for detecting and measuring the magnitude of an impact force applied to a container and more particularly to method and apparatus for simulating a glass container to detect and measure the impact forces to which a bottle is subjected in the filling line.

2. Description of the Prior Art

In a bottle filling line containers, such as glass bottles, are conveyed in virtual contact with one another from station to station at different speeds. At certain points in the filling line the bottle flow stops or is slowed causing impact between adjacent bottles and impact of the bottles with the guide rails that maintain the bottles on the conveying path. Consequently, the bottles experience a variety of impact forces applied at various points along the height of the bottle.

Devices for sensing and recording impact forces delivered to an object are well-known. U.S. Pat. Nos. 4,633,703 and 4,062,221 disclose impact sensing devices that utilize accelerometers for testing the operation of a shock absorber on an automobile. The accelerometer is mounted in a position to detect oscillations of the automobile and provide output signals to circuitry that indicate visually a record of the number of oscillations made by the vehicle. In this manner it is possible to indicate the condition of the shock absorber.

U.S. Pat. No. 3,380,294 discloses an inertial impact instrument used on space vehicles to measure the penetration resistance of the surface of an extraterrestrial body upon impact by a space vehicle. A hollow spherical shell contains three orthogonal decelerometers. The decelerometers are oriented and mounted to measure force components along the X, Y and Z axes. Output from the decelerometers in the form of a pulse signal is fed to oscillators where the signals are amplified and transmitted to an orbiting vehicle above the extraterrestrial body.

U.S. Pat. No. 3,020,875 discloses a device for detecting shocks in any direction in a plane perpendicular to a horizontal axis and in two directions in a plane perpendicular to a vertical axis. The indicator utilizes gauges having weights suspended from a rod which is mounted on a pin of a release mechanism.

U.S. Pat. No. 3,149,606 discloses an accelerometer that includes two weights positioned along different axes. The weights are spring-loaded against supports so that a non-axial acceleration at more than a given value will displace a respective weight from its support. The consequent position of the weight will show that a given acceleration has been exceeded.

While impact devices are known, and in particular impact devices that use accelerometers, none of the known devices disclose method and apparatus adaptable for detecting and measuring impact forces sustained by bottles in a glass filling line. The forces must be effectively measured regardless of the angle of impact. The measuring device must be responsive to a wide range of impact frequencies. Known devices are not readily adaptable to record frequencies of impact that are commonly sustained by bottles in the bottle filling operation. Therefore there is need for bottle testing apparatus capable of recording and measuring impact forces independent of the direction of application and at the frequency range experienced in a bottle filling operation.

SUMMARY OF THE INVENTION

In accordance with the present invention there is provided an impact sensor that includes a housing having a sidewall, a top wall, and a bottom wall forming an internal chamber. The top and bottom walls have openings therethrough to provide access to the chamber. A support member is centrally positioned in the internal chamber and is secured to the sidewall. Indicator means is retained on the support member in a position within the internal chamber for detecting an impact force applied to the housing. Means positioned in the housing and connected to the indicator means supplies electrical power to the indicator means to actuate the indicator means to convert the impact force applied to the housing to an electrical output signal having a value proportional to the magnitude of the impact force and representative of the direction of the impact force applied to the housing. Electrical circuitry connected to the indicator means receives the output signal from the indicator means and processes the output signal to obtain an indication of the magnitude of the impact force applied to the housing.

Further in accordance with the present invention there is provided a method for detecting the magnitude of an impact force applied to a container that includes the steps of positioning a sensor within a container for detecting an impact force applied externally to the container. The impact force detected by the sensor is converted to an electrical output signal having a value proportional to the magnitude of the impact force and representative of the direction of the impact force applied to the container. The electrical output signal is processed to obtain an indication of the magnitude of the impact force applied to the housing.

Additionally the present invention is directed to bottle testing apparatus that includes an impact sensor with a housing having a configuration simulating a bottle for testing. An impact indicator is positioned in the housing. Means is provided for supporting the impact indicator at a preselected location within the housing. Power means is connected to the impact indicator for actuating the impact indicator to convert an impact force applied to the housing to an output signal representative of the magnitude and direction of the impact force. Signal processing means connected to the impact indicator receives the output signal and generates a corresponding readout indicating the magnitude of the impact force applied to the housing.

Accordingly, the principal object of the present invention is to provide an impact sensor for detecting and measuring a horizontally directed force applied externally to a container.

Another object of the present invention is to provide method and apparatus for simulating a container in a filling line for detecting and measuring the impact forces applied to a container as it is conveyed along the filling line in a bottling operation.

An additional object of the present invention is to provide method and apparatus for simulating a glass bottle for non-destructive testing of the impact forces subjected to the glass bottle as it is conveyed along a filling line in the bottling process.

Another object of the present invention is to provide apparatus for detecting and measuring impact forces applied from any direction to a glass container and at a frequency range corresponding to the frequency of impacts applied to a glass container in a filling line.

These and other objects of the present invention will be more completely disclosed and described in the following specification, the accompanying drawings, and the appended claims.

DESCRIPTION OF THE PREFERRED EMBODIMENTS

Figure 1:
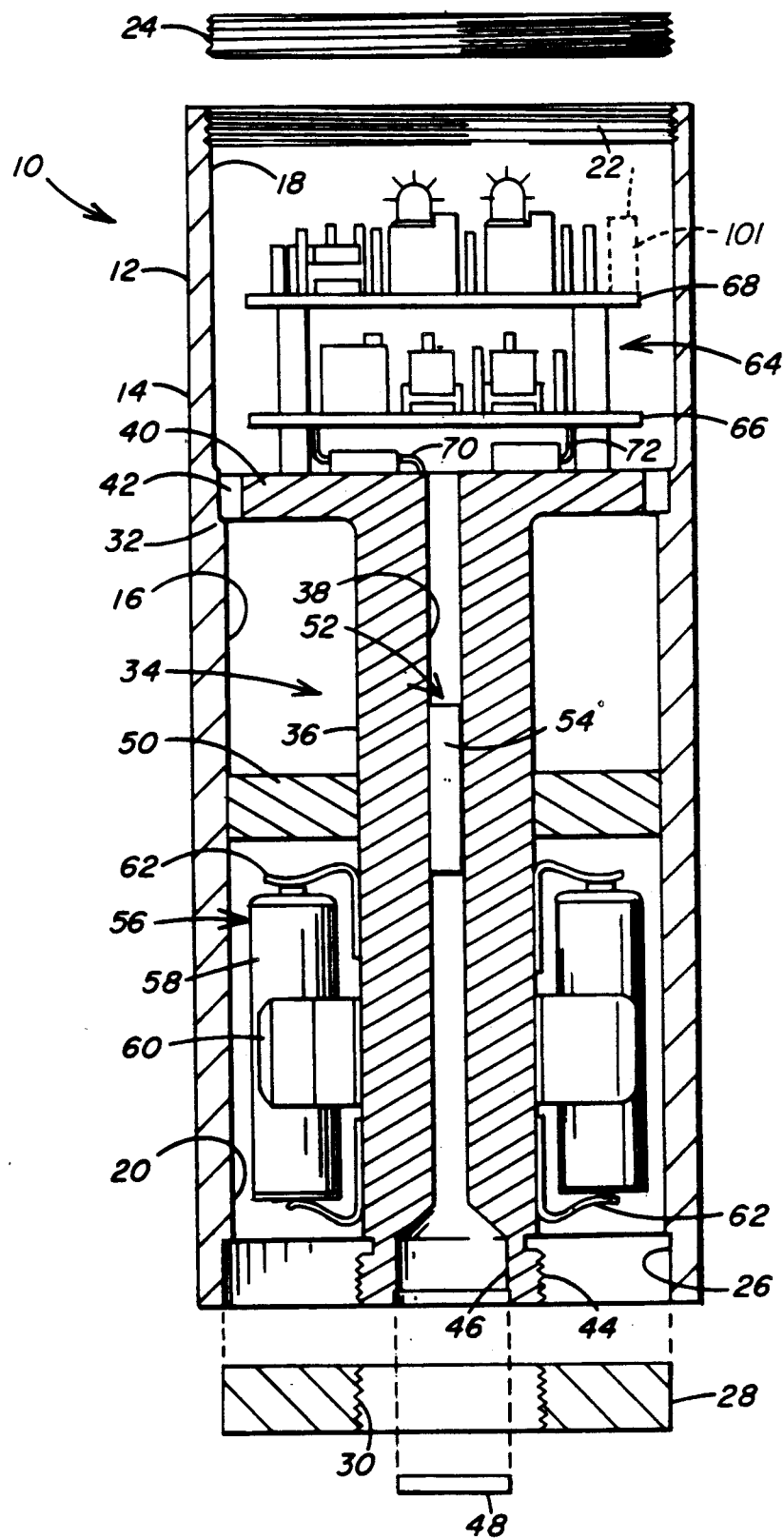
FIG. 1 is an exploded sectional view in side elevation of an impact sensor.

Referring to the drawings and particularly to FIG. 1, there is illustrated an impact sensor generally designated by the number 10 preferably having a configuration that simulates the configuration of a container, such as a glass bottle, that would be filled in a filling line as a part of a bottling operation. The configuration of the impact sensor 10 is selective in dimension based on the relative size of the container to be tested. For example the impact sensor can be constructed to simulate a 16 oz. non-returnable soda bottle, a pickle jar, a container for baby food, and glass containers for general use other than bottling food items.

In one application of the present invention the impact sensor 10 is representative of a soda bottle and therefore would be subjected to the forces encountered by a soda bottle as it is conveyed in the bottling operation. However it should be understood that the configuration and dimensions of the impact sensor are to be selected to conform to the type of container being tested.

In the example of a soda bottle the impact sensor 10 includes a housing 12 of a selected height and diameter. For a 16 oz. non-returnable soda bottle an appropriate outer diameter would be 3½ inches with an overall height of 6.75 inches. The housing 12 has a sidewall 14 of a thickness that provides the housing 12 with an acceptable degree of rigidity to withstand repeated impact forces. This permits non-destructive testing of a simulated glass container. Preferably the housing 12 is fabricated of a material capable of withstanding impact forces of a magnitude that exceeds the magnitude of the impact forces encountered in the bottling operation. A material for the housing 12 considered to be sufficiently rigid to withstand repeated testing is acrylic.

The housing sidewall 14 forms an internal chamber 16, an upper open end portion 18 and a lower open end portion 20. The housing 12 at the end portion 18 includes an internally threaded portion 22 for receiving an externally threaded cap 24 for closing the end portion 18. The threaded cap 24 also includes a center opening (not shown) for providing access to the portion of the chamber 16 beneath the cap 24 without having to remove the threaded cap. An enlarged internal bore 26 at the lower end portion 20 receives a base 28 for closing the lower end portion 20 and further making rigid the housing 12. The base 28 includes an axially located internally threaded bore 30.

The housing 12 includes on the sidewall 14 an internal shoulder 32 for receiving and locating axially within the chamber 16 a support member generally designated by the numeral 34. The support member 34 includes a center post 36 having an axial bore 38 therethrough. The center post 36 has an upper end portion which expands outwardly in a flange 40 having an annular edge portion 42 that is supported by the internal shoulder 32 of the housing sidewall 14. The opposite end portion of the center post 36 has an externally threaded portion 44 for receiving the base 28 for sealing the housing lower open end portion 20. The axial bore 38 of post 36 includes an enlarged portion 46 at the post threaded portion 44 for providing convenient access to the bore 38. The bore enlarged portion 46 is sealed by a plug 48 that is press fit onto an internal shoulder formed in the bore portion 46.

The support member 34 must have material strength and rigidity to resist vibration. Preferably the center post 36 forming the support member 34 is fabricated of nylon and has an octagonal cross sectional configuration. Located approximately intermediate the length of the center post 36 is a center ring 50 which is lightly press fit on the external surface of the center post 36. The center ring 50 may also be fabricated of nylon and having a preselected thickness as determined by the overall dimensions of the housing 12.

The center ring 50 together with the mounting of the flange 40 on the housing internal shoulder 32 serve to stabilize the support member 34 within the housing 12. As a result secondary vibrations of the housing 12 when impacted are reduced. The impact force applied to the housing 12 is transmitted directly to the center post 36.

Positioned within the support member axial bore 38 is an impact detector generally designated by the numeral 52. Preferably the impact detector 52 is retained on the support member 34 by positioning it within the bore 38 at the center of gravity of the housing 12. The impact detector 52 has a substantially elongated cylindrical housing 54 of a dimension that corresponds to the internal diameter of the bore 38 for a light press fit therein so that the detector 52 is maintained precisely in a preselected position within the bore 38.

The impact detector 52 is a commercially available accelerometer having a frequency response adaptable to measure impact forces applied to the housing 12 at a rate corresponding to the frequencies of impact subjected to glass containers in a bottle filling line. The operation of the accelerometer 52 is well-known and is beyond the scope of the present invention, and therefore will not be described in detail herein.

A commercially available piezoresistive accelerometer adaptable for use in the present invention is manufactured and sold by Entran Devices, Inc. under Model No. EGA2-R. This type of accelerometer is operable to sense an impact force applied externally to the housing 12 at an angle to the major axis of acceleration and convert the impact force into an electrical output signal comprising a first component representative of the magnitude of the impact force along the X-axis and a second component representative of the magnitude of the impact force along the Y-axis. These two components are detected and measured by twin units positioned back to back in a biaxial configuration within a cylindrical housing 54.

The accelerometer 52 is energized by a power source generally designated by the numeral 56 contained within the housing 12. A suitable power source 56 for powering the accelerometer 52 includes a plurality of batteries, such as 3.4 volt AA lithium batteries 58. The batteries are retained within the internal chamber 16 below the center ring 50 by a battery holder 60 mounted on the center post 36. Preferably the battery holder 60 includes spring clips 62 that are positioned to space the batteries 58 an equal distance apart around the center post 36. The batteries 58 are connected by conductors (not shown) to the impact indicator 52.

The impact detector 52 in the form of a biaxial accelerometer is operable to detect impacts applied to the exterior of the housing 12 at very short durations, which is generally the nature of the impact forces experienced by a glass bottle as it is conveyed in the bottling operation. In addition the impact detector 52 is radially isotropic in that it generates an output signal which is representative in magnitude of the impact force independent of the angular direction of the impact force applied to the housing 12.

In response to the impact force applied to the housing 12 the impact detector 52 transmits by electrical conductors (not shown) an electrical output signal having a value which is proportional to the magnitude of the impact force and representative of the direction of the impact force applied to the housing. The output signal from the detector 52 includes a first component representative of the impact force vector along the X-axis and a second component which is representative of the impact force vector along the Y-axis. The output signal is transmitted by the conductors to electrical circuitry generally designated by the numeral 64 supported by the center post flange 40 within the upper portion of the chamber 16.

Figure 2:
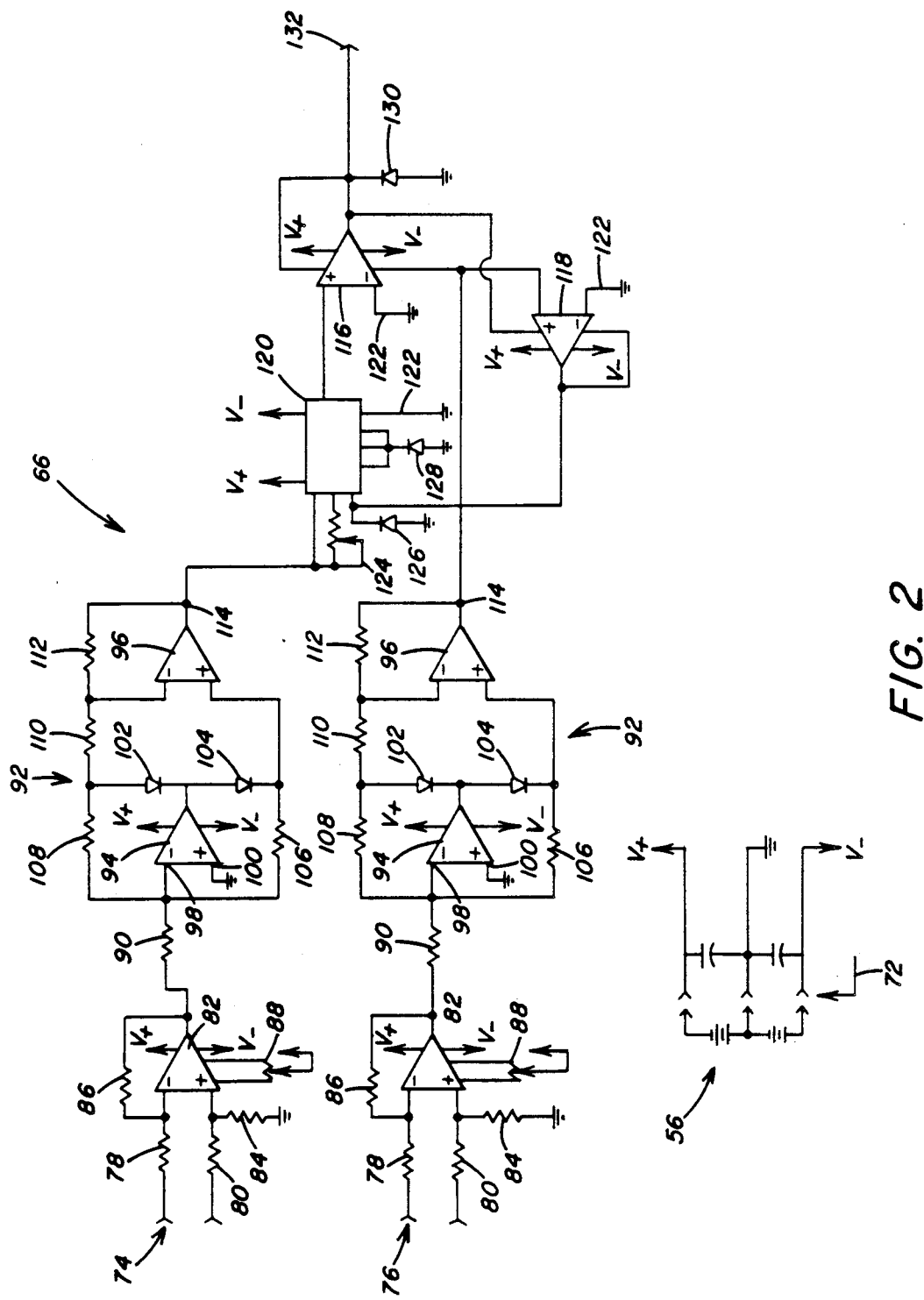
FIG. 2 is an electrical schematic of the circuitry contained within the impact sensor shown in FIG. 1 for generating a signal representative of the force applied to the impact sensor.
Figure 3:
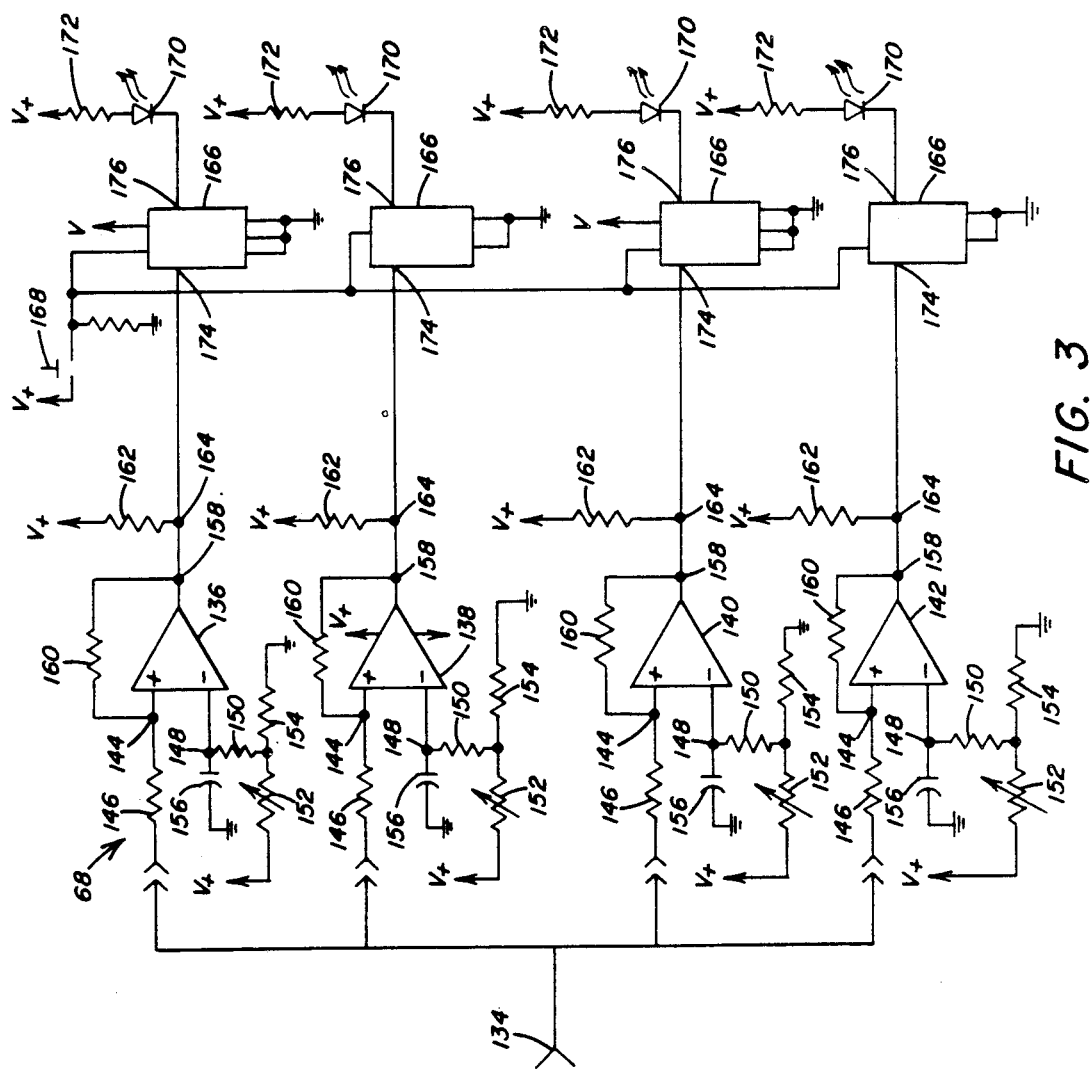
FIG. 3 is a view similar to FIG. 2, illustrating the circuitry for analyzing the signal from the circuitry shown in FIG. 2 to obtain an indication of the magnitude of the force applied to the impact sensor.

The electrical circuitry 64 is illustrated schematically in FIGS. 2 and 3. As illustrated in FIG. 1 the circuitry 64 includes a first circuit board 66 securely mounted on the flange 40 and a second circuit board 68 securely mounted above the first board 66. In accordance with the present invention the circuitry of the first board is illustrated in FIG. 2, and the circuitry for the second board is illustrated in FIG. 3.

The circuitry of the boards 66 and 68 is electrically connected to each other. The purpose of the first circuit board 66 is to vectorially add the differential inputs of the output signal from the impact indicator 52. As well known with a biaxial accelerometer the output signal is conditioned to generate an electrical equivalent of the X and Y components of the impact force applied to the housing 12.

Now referring to FIG. 2 there is illustrated the components that form the first circuit board 66. The board 66 provides the impact sensor 10 with radial isotropy in which the output signal from the indicator 52 is transmitted in two force vector components by lead 70, shown in FIG. 1 to input terminals generally designated by the numerals 74 and 76 in FIG. 2. The board 66 is supplied with power from the batteries 58 through lead 72. The input signals are transmitted through resistors 78 and 80 respectively to a differential amplifier 82. Each resistor 80 is connected by a resistor 84 to ground and resistor 78 is connected to a resistor 86 connected between the output and input to the amplifier 82.

The amplifier 82 is operable to balance out any errors in the differential bridge circuit of the biaxial accelerometer. Any variation in the modeled resistance values represents a DC voltage which must be balanced to zero volts. This is accomplished by a zero adjust potentiometer 88. In this manner it is assured that equivalent impact forces spaced 180° apart will provide equal results.

The resistors 84 and 86 function as differential resistance pairs to balance the two accelerometers comprising the impact detector 52 for equivalent impacts. The values for the resistor pairs 84 and 86 vary with the specifications of the accelerometers and are determined empirically with impacts 90° apart. The voltage applied to the first circuit board comes from the battery power supply 56 through lead 72 which is also schematically illustrated in FIG. 2.

Once the input signals to the first circuit board 66 from the impact detector 52 are conditioned they are transmitted as output from the amplifiers 82 through resistor 90 to a rectifier circuit generally designated by the numeral 92. The rectifier circuit 92 includes a dual arrangement of amplifiers 94 and 96.

Amplifier 94 includes an input terminal 98 connected to the output of amplifier 82 and a grounded input terminal 100. The output from amplifier 94 is connected to the input of amplifier 96 through the pair of diodes 102 and 104 and the resistors 106, 108, and 110. Resistor 112 connects the output terminal of amplifier 96 with the negative input terminal thereof. The amplifier pairs 94 and 96 are operable to provide output signals at terminal 114 at a voltage value that will permit the vector addition of the X and Y force components of the detected impact force. The negative voltages are rectified by the above arrangement before the vector addition operation is performed.

The positive voltage signals from the amplifier output terminals 114 are transmitted to the amplifiers 116 and 118 and the multifunction converter 120 for vector addition of the signals from the terminals 114. The amplifiers 116 and 118 and the converter 120 are also connected to the power source 56 and grounded connections 122. The converter 120 is also connected to potentiometer 124 and grounded diodes 126 and 128. Output from the amplifier 116 is connected to a grounded diode 130 and amplifier 118. The output from amplifier 118 is also connected to the grounded diode 126 at the input to the converter 120.

The converter 120 is operable to perform logarithmic functions such as LOG, LOG RATIO and ANTI-LOG. Thus the converter and amplifier pairs 116 and 118 vectorially add the two accelerometer signals from the rectifier circuit 92 to generate a resultant output signal at terminal 132 which is introduced as input at terminal 134 shown in FIG. 3 to the circuitry of the second board 68.

The circuitry of the second board 68 includes four parallel positioned comparators 136-142 for receiving the output voltage signal from the first board 66 at terminal 134 and comparing it to the preset level of the respective comparator 136-142. Each comparator 136-142 is set for a desired impact level, and is connected at a positive input terminal 144 through a resistor 146 to the terminal 134. Negative input terminal 148 of each comparator 136-142 is connected through a resistor 150 to a potentiometer 152 which is, in turn, connected through a resistor 154 to ground. Also the negative input terminal 148 of each comparator is connected through a capacitor 156 to ground. Each potentiometer 152 is set at a different level to provide a different input voltage at the respective terminals 148 to be compared to the magnitude of the detected impact force applied to the housing 12 and represented by the output voltage at terminal 134.

The output voltage from the circuitry of the first board 66 is received at input terminals 144 and is compared to the preset voltage signal at input terminals 148. If the applied input voltage at terminal 144 exceeds the preset voltage from the potentiometer 152, then a positive voltage signal is transmitted from the comparator output terminal 158. If, for example, the magnitude of the input signal to terminal 144 is less than the magnitude of the preset signals for all of the comparators, except for comparator 136, then an output signal appears only at terminal 158 of comparator 136.

The applied input signal at terminal 134 may exceed the levels of the preset signal for comparators 136 and 138, but not for the other two comparators 140 and 142. In that case, a signal would be recorded at the output terminals 158 of comparators 136 and 138. Also it should be noted that the output terminal 158 of each comparator is connected through a resistor 160 to the positive input terminal 144 and also through resistor 162 at terminal 164 to the power source 56 shown in FIG. 1.

Each of the comparators 136-142 at the output terminal 58 thereof is connected to a logic latch 166. Each of the latches 166 is connected to ground and to a switch 168 positioned on the second circuit board 168 in a position permitting convenient access through the opening (not shown) in the cap 24 permitting the switch 168 to be triggered without having to remove the threaded cap 24. Each latch 166 is connected to a light emitting diode 170 which is, in turn, connected through a resistor 172 to the power supply 56.

The latches 166 are normally maintained nonconductive. In the event an output signal is transmitted from the respective terminal 158 at the output of the corresponding comparator, a signal is received at input terminal 174 of the corresponding latch 166. The presence of a signal at the latch input terminal 174 switches the latch from a non-conductive state to a conductive state. As a result, a signal is transmitted from output terminal 176 of the latch to the diode 170. The diode is actuated and illuminated to indicate that the impact force delivered to the housing 12 has exceeded a predetermined magnitude. Thus each diode 170 is operable to illuminate when the voltage at terminal 134 exceeds the set point voltage of the corresponding one of the comparators 136-142. The diode remains illuminated until the switch 168 is closed. When the switch 168 is closed each actuated logic latch 166 is reset.

In the embodiment of the present invention illustrated in FIG. 1, signal processing is accomplished by the circuitry 64 contained within the impact sensor 10. It should also be understood that the signal processing can take place at a location removed from the housing 12. With this embodiment the output signal from the impact detector 52 is transmitted from the sensor housing 12 through optional transmitting means 101, shown in chain line in FIG. 1, to a control station where the electrical circuitry 64 is located. The control station can, for example, include the first and second circuit boards 66 and 68 described above in which the light emitting diodes 170 are actuated as above described to indicate the severity of the force applied to the sensor housing 12. It should be further understood that the output signal from the impact detector 52 can be transmitted to a microprocessor located on the housing 12 or at the control station. The microprocessor is programmed to analyze the output signal from the impact detector 52. The microprocessor converts the output signal to a digital readout indicating numerically the magnitude of the applied impact force. This is compared to the embodiment in which the magnitude of the impact force is indicated by actuation of the light emitting diodes 170.

According to the provisions of the patent statutes, we have explained the principle, preferred construction and mode of operation of our invention, and have illustrated and described what we now consider to represent its best embodiments. However, it should be understood that within the scope of the appended claims the invention may be practiced otherwise than as specifically illustrated and described.

We claim:

1. An impact sensor comprising,
   a housing having a sidewall forming an internal chamber, a top wall and a bottom wall, said top and bottom walls each having openings therethrough to provide access to said chamber,
   a support member centrally positioned in said internal chamber and secured to said sidewall,
   detector means retained on said support member in a position within said internal chamber for detecting an impact force applied to said housing
   means positioned in said housing and connected to said detector means for supplying electrical power to said detector means to actuate said detector means to convert the impact force applied to said housing to an electrical output signal having a value proportional to the magnitude of the impact force and representative of the direction of the impact force applied to said housing, and
   electrical circuitry connected to said detector means for receiving the output signal from said detector means and processing the output signal to obtain an indication of the magnitude of the impact force applied to said housing.

2. An impact sensor as set forth in claim 1 in which,
   said support member includes a center post axially positioned in said housing, and
   said detector means is retained at the center of gravity of said housing on said center post.

3. An impact sensor as set forth in claim 1 which includes,
   said housing having a sidewall with a thickness and configuration representative of a glass bottle, and
   means for supporting said support member on said sidewall to transmit the impact force applied to said housing through said sidewall and said support member to said detector means.

4. An impact sensor as set forth in claim 1 in which,
   said detector means includes an accelerometer for generating an output signal in response to the impact force and having a measurable value representative of the magnitude and angle of impact of the force applied to said housing.

5. An impact sensor as set forth in claim 1 in which,
   said electrical circuitry includes means for processing the output signal to generate a corresponding signal indicating the magnitude of the impact force for any impact angle.

6. An impact sensor as set forth in claim 1 which includes,
   a plurality of light emitting diodes mounted within said housing chamber and connected to said electrical circuitry to receive the output signal, and
   each of said light emitting diodes being actuated to indicate the magnitude of the applied impact force when the output signal exceeds a value corresponding to the voltage at which the respective light emitting diode is actuated.

7. An impact sensor as set forth in claim 1 which includes,
means for transmitting the output signal to a location removed from the housing for measuring and recording the magnitude of the impact force.

8. A method for detecting the magnitude of an impact force applied to a moving container comprising the steps of,
positioning a sensor within a movable container at the center of gravity of the container for detecting an impact force applied externally to the container during movement of the container,
converting the impact force detected by the sensor to an electrical output signal having a value proportional to the magnitude of the impact force and representative of the direction of the impact force applied to the container, and
processing the electrical output signal to obtain an indication of the magnitude of the force applied to the container.

9. A method as set forth in claim 8 which includes, transmitting the impact force through the container at the sensor.

10. A method as set forth in claim 8 which includes,
generating the output signal to include the X component and the Y component of the force vector of the impact force applied to the container at any angle of impact,
vectorially adding the X and Y components to obtain a resultant signal, and
comparing the resultant signal to preset values corresponding to predetermined magnitudes of impact force to identify the severity of the impact force.

11. A method as set forth in claim 8 which includes, using a biaxial accelerometer as the sensor.

12. A method as set forth in claim 8 which includes,
comparing the output signal to a series of reference points each presenting an impact force of a selected magnitude, and
actuating on the container a light emitting diode associated with each reference point to indicate that the impact force has reached the magnitude required to actuate the respective diode.

13. A method as set forth in claim 8 which includes,
generating a readout on the container responsive to the output signal to record the magnitude of the impact force applied to the container.

14. A method as set forth in claim 8 which includes,
transmitting the output signal to a location removed from the container, and
converting the output signal to a readout identifying the magnitude of the impact force applied to the container.

15. Bottle testing apparatus comprising,
an impact sensor including a housing having a configuration and center of gravity simulating a bottle for testing,
an impact detector positioned in said housing at the center of gravity,
means for supporting said impact detector within said housing,
power means connected to said impact detector for actuating said impact detector to convert an impact force applied to said housing to an output signal representative of the magnitude and direction of the impact force, and
signal processing means connected to said impact detector for receiving the output signal and generating a corresponding readout indicating the magnitude of the impact force applied to said housing.

16. Bottle testing apparatus as set forth in claim 15 which includes,
means for transmitting the impact force applied externally to said housing at any angle to said impact detector.

17. Bottle testing apparatus as set forth in claim 15 in which,
said signal processing means includes first electrical means for adding the X and Y components of the force vector representing the impact force to obtain a resultant signal, and
second electrical means for converting said resultant signal to a quantative indication of the magnitude of the impact force.

18. Bottle testing apparatus as set forth in claim 15 in which,
said signal processing means is positioned on the impact sensor.

19. Bottle testing apparatus as set forth in claim 15 which includes,
means for resetting said signal processing means after the impact force is converted to said output signal to record successive impacts applied to said housing.

20. Bottle testing apparatus comprising,
an impact sensor including a housing having a configuration and center of gravity simulating a bottle for testing,
an impact detector positioned in said housing at the center of gravity,
means for supporting said impact detector at the center of gravity within said housing,
power means connected to said impact detector for actuating said impact detector to convert an impact force applied to said housing to an output signal representative of the magnitude of the impact force, and
means for transmitting the output signal to a control station removed from said impact sensor where such signal can be stored and converted into a digital readout of the magnitude of the impact force.

* * * * *

UNITED STATES PATENT AND TRADEMARK OFFICE
CERTIFICATE OF CORRECTION

PATENT NO. : 4,989,462

DATED : February 5, 1991

INVENTOR(S) : MICHAEL W. DAVIS, LEONARD J. WEILAND, MARK F. ZANELLA

It is certified that error appears in the above-identified patent and that said Letters Patent is hereby corrected as shown below:

Column 7, line 22, change "58" to --158--.

Signed and Sealed this

Thirtieth Day of June, 1992

Attest:

DOUGLAS B. COMER

Attesting Officer     Acting Commissioner of Patents and Trademarks